June 23, 1964 E. FANICK Plant Pat. 2,412
ASH TREE
Filed May 28, 1962 2 Sheets-Sheet 1
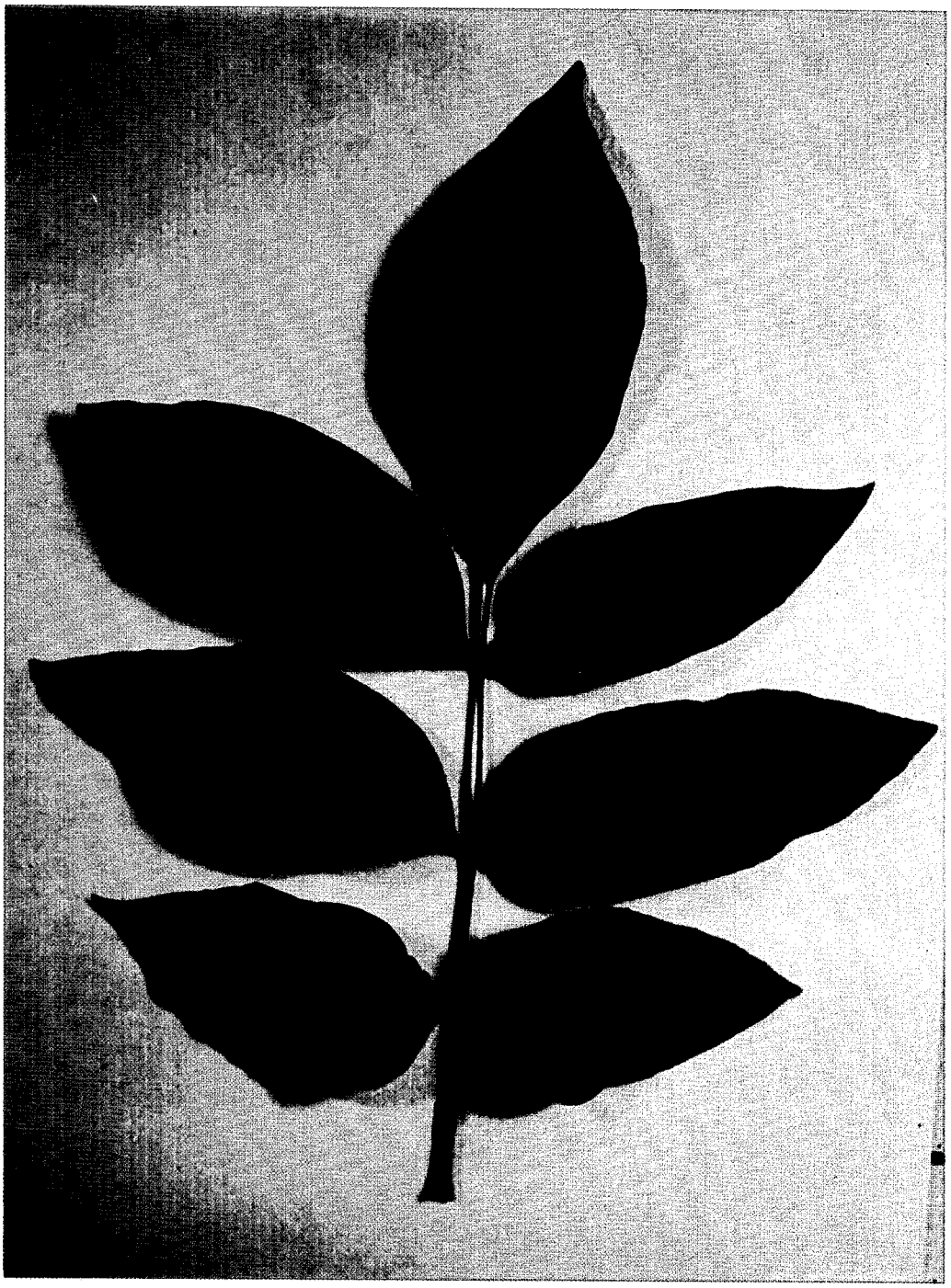
INVENTOR
EDDIE FANICK
BY Browning, Simms, Hyer & Eickemroht
ATTORNEYS June 23, 1964 E. FANICK Plant Pat. 2,412
ASH TREE
Filed May 28, 1962 2 Sheets-Sheet 2
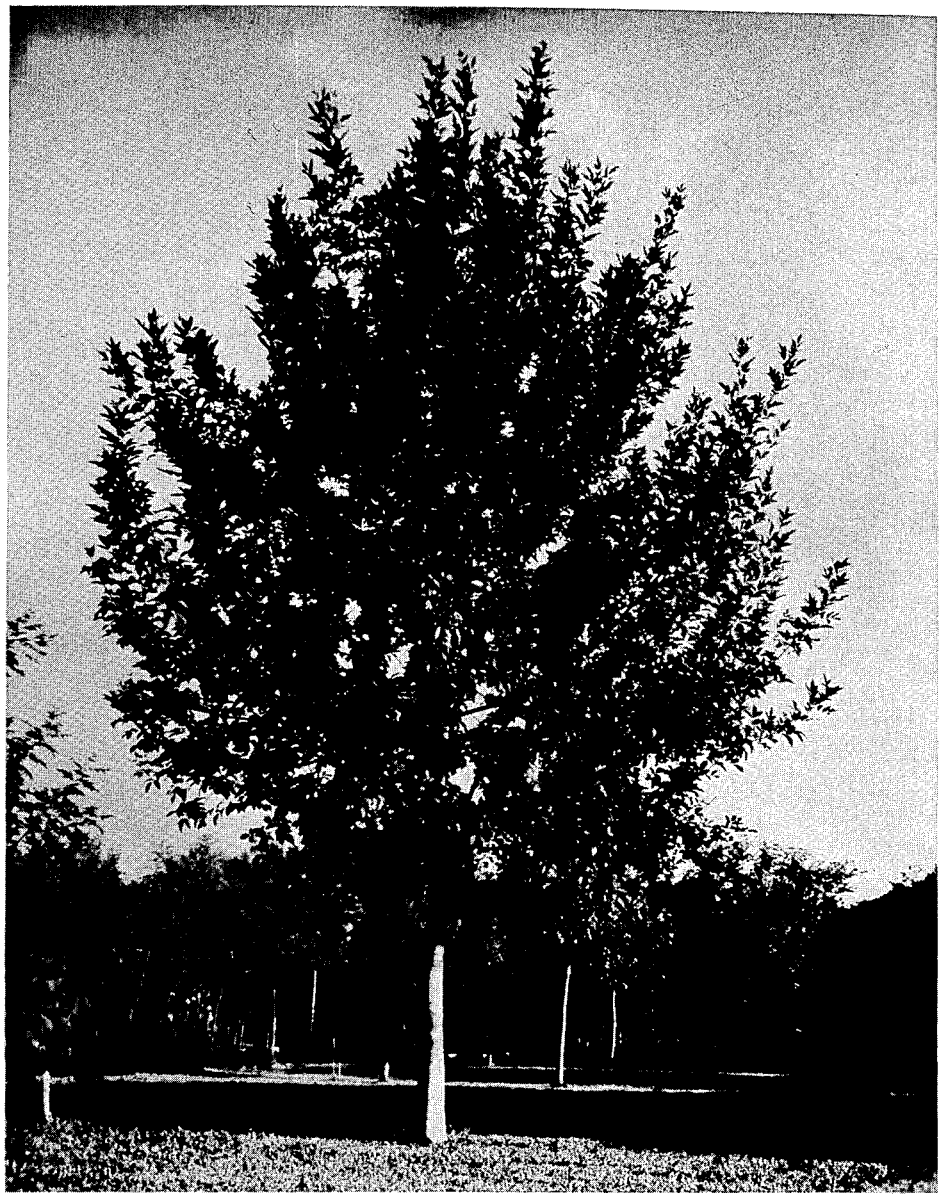
Eddie Fanick
INVENTOR.
BY Browning, Simms
Dyer & Eichenrodt
ATTORNEYS United States Patent Office Plant Pat. 2,412
Patented June 23, 1964

2,412
ASH TREE

Eddie Fanick, 1025 Holmgreen Road, San Antonio, Tex.

Filed May 28, 1962, Ser. No. 198,386
1 Claim. (Cl. Plt.—51)

My new discovery relates to a new seedling variety of ash tree of the species *Fraxinus velutina.*

My new ash tree was discovered by me in San Antonio, Texas. A lot of Rio Grande ash (*Fraxinus velutina*) seeds were sown by me in a cultivate area and from this sowing, I discovered the seedling of my new variety. It is possible my new ash tree is a sport or mutation of the Rio Grande ash or it could be a hybrid with Mexican ash, *Fraxinus berlandieriana.*

One outstanding characteristic of my new ash tree is its large, dark green leaves. Its leaves are larger than those of the Rio Grande ash and *Fraxinus velutina,* Arizona variety, and the leaves do not wind burn or fade in hot weather. Moreover, the leaves of my ash do not yellow in soils which have been over-limed or otherwise have excess alkalinity, as do the leaves of many other varieties of ash. This characteristic may possibly be attributed to the fact that the leaves are thick and leathery as compared to other ash leaves. The leaves of my new ash tree are glossy and, in comparison to the leaves of fourteen other varieties of ash tree (from different sections of the United States) also growing in my nursery, they are more resistant to leaf spot fungus.

The number of leaflets are the same as those of all *Fraxinus velutina;* that is, normally there are five, sometimes three or seven per leaf stem. The leaves are arranged in an opposite manner with three to four inches between nodes, the internodal distance sometimes being as much as six inches.

Another important characteristic of my new ash tree is its fast growth. This characteristic, combined with that of the large green leaves, makes it a most desirable shade tree and further, its compatability with alkaline soils makes it even more desirable for the hot, dry climates of the western states.

My new ash tree has a dense, compact growth with sturdy limbs which are resistant to breakage in wind storms.

The original illustrations accompanying this specification show a full view of my new tree and also a view of one of its leaves.

Following is a detailed description of this new variety:

Growth habits: Similar to those of the Rio Grande ash but considerably more vigorous in that it grows 25% faster. It tolerates hot, dry climates such as in New Mexico where it has been grown and yet will do well in more temperate climates such as in California where it has been grown. It is winter hardy, having undergone zero temperature conditions in my nursery in San Antonio. I have observed that in my nursery among other ash trees such as, to name a few, Modesto ash, Montebello ash, Arizona ash, Moraine ash, Escandido ash and Mexican ash, my ash tree is the first of all varieties of ash to leaf out and is the last to drop its leaves in the fall.

Foliage: Abundant.

Leaflets: Number is normally five, although sometimes occurring with three to seven, per leaf stem.

*Color.*—Closest to Ivy Green, 0001060/3 British Colour Council by Wilson, 1941; specifically, a deep, dark green, greener than other ash trees.

*Size.*—Large, mature leaflets averaging two inches across and four inches long.

*Shape.*—Blades are ovate.

*Texture.*—Leathery and thick but glossy.

*Edge.*—Entire to finely serrated.

Stems: Leaf stems are long and slender but adequately strong to support leaves without unusual drooping. Color—green.

Bark: After the third year from budding, the trunk turns silvery in color. The bark is relatively smooth with small nodules randomly situated thereon.

Reproductive organs: My ash is staminate but is not seeding as determined by observation of a specimen for six years.

I have asexually reproduced this variety of ash by budding in my nursery and its distinguishing characteristics have proved to be firmly fixed.

Having thus disclosed my discovery, I claim:

A new variety of ash tree (*Fraxinus velutina*), substantially as shown and described, characterized particularly by its large, glossy, dark green leaves; its fast growth compared with other varieties of ash trees; its light silvery bark on its trunk after the third year from budding; its early leafing habits in the spring and its late retention of leaves in the fall; its tolerance to heat, drought and alkaline soils; and its dense, compact growth with sturdy limbs resistant to breakage in wind storms.

No references cited.